United States Patent [19]
Frey et al.

[11] Patent Number: 5,851,400
[45] Date of Patent: Dec. 22, 1998

[54] METHOD FOR ELIMINATING THE DISPLACER IN DISPLACEMENT CHROMATOGRAPHY OF PROTEINS

[75] Inventors: Douglas D. Frey; John C. Strong, both of Baltimore, Md.

[73] Assignee: University of Maryland at Baltimore County, Baltimore, Md.

[21] Appl. No.: 821,904

[22] Filed: Mar. 21, 1997

[51] Int. Cl.$^6$ .................................................. B01D 15/08
[52] U.S. Cl. ...................... 210/635; 210/656; 210/198.2; 530/413; 530/416; 530/417
[58] Field of Search .................................. 210/635, 656, 210/659, 198.2; 530/413, 416, 417

[56] References Cited

U.S. PATENT DOCUMENTS

| | | | |
|---|---|---|---|
| 5,427,686 | 6/1995 | Asher | 210/635 |
| 5,439,591 | 8/1995 | Pliura | 210/635 |
| 5,545,328 | 8/1996 | Pliura | 210/635 |

OTHER PUBLICATIONS

Frey, A.IchE J., vol. 41 No. 5, pp. 1171–1183, 1995.
Frey, Biotechnol. Progress, vol. 12, No. 1 pp. 65–73, Feb. 16, 1996.

*Primary Examiner*—Ernest G. Therkorn
*Attorney, Agent, or Firm*—Benjamin Aaron Adler

[57] ABSTRACT

The present invention provides a method for eliminating the use of a displacer in displacement chromatography of proteins. Elimination of displacer is accomplished by producing an appropriate retained pH gradient using adsorbed buffering species. When the band velocity curves of the proteins under consideration intersect a vertical section of the pH profile and none of these protein have adsorption isotherm which cross each other at the pH of the intermediate plateau, and when the amount of protein in the feed slug to the column is such that bands of the appropriate concentration are formed in the displacement train, then a displacement pattern results in a chromatography column even though no displacer is present.

11 Claims, 7 Drawing Sheets

FIGURE 1 (©1981 Csaba Horvath)

FIGURE 2 (©1981 Csaba Horvath)

METHOD FOR ELIMINATING THE DISPLACER IN DISPLACEMENT CHROMATOGRAPHY OF PROTEINS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

This invention was produced in part using funds obtained through a grant from the National Science Foundation. Consequently, the federal government has certain rights in this invention.

1. Field of the Invention

The present invention relates generally to chemistry and biochemistry. Specifically, the present invention relates to the preparative purification of biopolymers using chromatography.

2. Description of the Related Art

The earliest workers to investigate the technique of displacement chromatography were Tiselius and Claesson (S. Claesson, *Ark. Kem., Mineral. Geol.*, 23A:1 (1947); A. Tiselius, *Ark. Kent., Mineral. Geol.*, 16A:1 (1943)), who both investigated the use of the technique for analytical-scale separations. For this reason, the early scientific literature generally refers to the technique as displacement analysis. The subsequent development of linear elution chromatography by Martin and co-workers (A. J. P. Martin and R. L. M. Synge, *Biochem. J.*, 35:1358 (1941); R. Consden, et al., *Biochem. J.* 38:224 (1944); and A.T. James and A. J. P. Martin, *Biochem. J.* 50:679 (1952)), however, soon overshadowed the earlier work, and the technique of displacement chromatography went largely unpracticed.

In the early 1980s, Horvath and co-workers at Yale University recognized the utility of displacement chromatography for preparative- and process-scale chromatography; i.e., chromatography where the objective is to collect purified solutes. These workers employed ion exchange column packings and high performance liquid chromatography (HPLC) equipment (Horvath, A. Nahum, and J. Frenz, *J Chromatogr.*, 218:365 (1981)). The choice of HPLC equipment largely eliminated the existence of axial dispersion due to the use of small adsorbent particles of less than 10 $\mu$m in diameter. Early work by Horvath and co-workers emphasized the separation of small molecules, such as phenols and phenylacetic acids (Horvath, A. Nahum, and J. Frenz, *J. Chromatogr.*, 218:365 (1981)), but soon displacement techniques for separating peptides (S. M. Cramer and Cs. Horvath, *Preparative Chromatogr.*, 1:29 (1988)) and proteins (A. W. Liao, et al., *Chromatographia*, 24:881 (1987)) were investigated.

Subsequent work by Cramer and co-workers at Rensselaer Polytechnic Institute emphasized protein separations using ion exchange adsorbents, primarily because of the importance of this class of separation processes in the biotechnology industry (C. A. Brooks and S. M. Cramer, *AIChE J.*, 38:1969 (1992); C. A. Brooks and S. M. Cramer, *AIChE J.*, 38:1969 (1992); and S. D. Gadam, et al., *J. Chromatrogr.*, 630:37 (1993)). Of special interest to these last workers was the development of novel displacer components including dendritic polymers, protected amino acids, and related types of low-molecular weight species.

One objective of using these types of novel displacers was partly to address some of the key disadvantages of displacement chromatography; namely, the need for employing a displacer component which may potentially contaminate the components which are to be separated, and the difficulties inherent in removing the displacer from the column after the displacement step. The difficulty in removing the displacer arises due to the fact that the displacer is generally the most strongly-bound adsorbate present.

The theory of displacement chromatography was developed further by Glueckauf (E. Glueckauf, *Disc. Faraday Soc.* 7:12 (1949)) in 1949, with subsequent theoretical work performed by many workers (see, e.g., S. Golshan-Shirazi, et al., *Anal. Chem.*, 61:1960 (1989)). The basic operation of displacement chromatography is described in FIG. 1, taken from Horvath, et al., *J. Chromatogr.*, 218:365 (1981). As shown in the figure, the traditional method to perform displacement chromatography is to first equilibrate a column of adsorbent particles with the carrier (i.e., solvent), and then inject a feed slug containing the solutes to be separated dissolved in the solvent. Next, a solution containing the solvent and a displacer component is pumped into the column in order to "push" the feed components through the column as well as to form the displacement train containing separated feed components. Finally, the displacer component is removed from the column using a regenerant solution, and the column is re-equilibrated with the carrier.

FIG. 2, also taken from Horvath, et al., *J. Chromatogr.*, 218:365 (1981), illustrates the relation between the adsorption isotherm of the displacer component and those of the feed components in order for the displacer to produce a so-called isotachic final pattern where each feed component is present as a pure component in a rectangular-shaped solute band. As shown in the figure, as a general rule the adsorption isotherm of the displacer component must overlie completely the isotherms of the feed components in order for this to occur; i.e., the displacer must be the most strongly-bound adsorbate present. In addition, as also shown in FIG. 2, the isotherms of the various feed components should not intersect each other.

In the late 1970s, Sluyterman and co-workers developed a form of ion-exchange chromatography, termed chromatofocusing, which employs a retained, internally-produced pH gradient (L. A. AE. Sluyterman and O. Elgersma, *J. Chromatogr.*, 150:17 (1978)). Chromatofocusing combines the resolving power of isoelectric focusing and the simplicity of ion-exchange chromatography to yield a separation method capable of high resolution. In addition to analytical applications, this mode of chromatography is in principle well-suited for preparative separations since it can accommodate large feed slugs (i.e., volume overloading), and since it can separate and concentrate proteins in a single step. Furthermore, among chromatographic techniques involving pH gradients, chromatofocusing tends to be the least denaturing since the method limits the amount of time proteins are exposed to pH extremes.

Despite the apparent suitability of chromatofocusing for preparative-scale separations, the current practice of the technique suffers from several limitations which hinder its use on a large scale. Perhaps the major limitation is the prohibitively high cost of the proprietary column packing and polyampholyte buffer system currently used in the method. In addition, polyampholyte buffers contain components which have been reported to associate with proteins, necessitating an additional polyampholyte removal step to recover the purified protein. Moreover, polyampholyte-containing buffers produce a linear pH gradient over a wide pH range. While such a gradient is useful for analytical separations, it is not necessarily the optimal gradient shape for a preparative separation where one target protein is being separated from various contaminants in a multicomponent mixture.

In order to avoid the difficulties associated with chromatofocusing just described, a number of workers have investigated the use of multicomponent mixtures of well-defined buffering species to replace the polyampholyte elution buffer in various applications of chromatofocusing (see, e.g., M. T. W. Hearn and D. Lyttle, *J. Chromatogr.*, 218:483 (1981)). In particular, if a limited number of strategically chosen buffering species is employed in the elution buffer, the target protein can be eluted as a focused band on a stepwise pH transition in order to separate it from impurities which elute elsewhere on the pH gradient (D. D. Frey, et al., *AIChE J.*, 41:1171 (1995)).

In previous work in the laboratory of the inventor of the present invention, a numerical method for simulating the formation of retained, stepwise pH transitions in an ion-exchange column was developed and used to investigate the focusing behavior of dilute protein mixtures when simple buffer systems containing multicomponent mixtures of well-defined buffering species were employed (D. D. Frey, et al., *AIChE J.*, 41:1171 (1995); and D. D. Frey, *Biotechnol. Progress*, 12:65 (1996)). In addition, optimized buffer compositions for producing retained pH gradients were described which eliminated the need for using a weak-base ion-exchange adsorbent having a buffering capacity. In particular, it was shown that if the column is presaturated with a buffering species having a pKa higher than any of the buffering species present in the elution buffer, and if this buffering species has an ionic form with is adsorbed by the ion exchange column packing, then a stable pH gradient consisting of a series of step-wise pH transitions is formed when the column is eluted with an elution buffer containing other adsorbed buffering species.

Other relevant previous work includes the process of "heater-displacer" gas-phase chromatography, in which a traveling heater is used to perform displacement chromatography in the gas phase (Badger, C.M.A., et al., *J. of Chrom.*, 126:11 (1976)), and the amino acid separation technique described by Carta et al, *AIChE Symposium Series*, No. 264, 84:54 (1988), in which displacement separation of amino acids is accomplished using a 0.01M NaOH solution as the displacer. Both of these techniques involve extreme conditions (i.e., extreme temperature or pH), which is generally incompatible with protein purification.

Thus, the prior art is drawn to methods of displacement chromatography using displacers that may have unsuitable equilibrium absorption properties or may contaminate the components to be purified. The present invention avoids the inefficiencies associated with the use of a displacer component, using instead a retained pH gradient formed with properly-formulated presaturation and elution solvents containing appropriate buffer species. Thus, the present invention fulfills a long-standing need and desire in the art.

SUMMARY OF THE INVENTION

One object of the present invention is to provide a method for eliminating the use of a displacer in displacement chromatography. This is accomplished by producing an appropriate retained pH gradient using adsorbed buffering species. When the band velocity curves of the proteins under consideration intersect a vertical section of this pH profile, and none of these protein have adsorption isotherm which cross each other at the pH of the intermediate plateau, and when the amount of protein in the feed slug is such that bands of the appropriate concentration are formed in the displacement train, then a displacement pattern results in the chromatography column even though no displacer is present.

In an embodiment of the present invention, there is provided a method of displacement chromatagraphy for the separation of proteins, comprising the steps of: selecting an adsorbed buffering species to produce an appropriate retained pH gradient having a pH profile, wherein band velocity curves of proteins to be separated intersect a vertical section of said pH profile, wherein all adsorption isotherm of said proteins to be separated are convex, and wherein none of said proteins to be separated have adsorption isotherm which cross another of said proteins' adsorption isotherm at a pH of an intermediate plateau; and supplying an amount of said proteins to be separated in a feed slug to produce high enough concentrations of said proteins to result in a displacement train, that, on said intermediate pH plateau, a step change in concentration from a zero level to a level in a protein band has a same velocity as a retained pH gradient.

In yet another embodiment of the present invention, there is provided a method of displacement chromatagraphy for the separation of proteins, comprising the steps of: presaturating a chromatography column by perfusing said chromatography column with a mixture of solvent and a buffering species titrated with a strong acid or strong base to an appropriate presaturation pH, wherein said chromatography column is packed with either a strong-acid cation exchange adsorbent or strong-base anion exchange adsorbent; injecting a feed slug containing solutes to be separated into said chromatography column; perfusing said chromatography column with an appropriate elution buffer to produce a column effluent; detecting separated proteins in said column effluent; and collecting said separated proteins.

In a preferred embodiment of the present invention, the solvent used is water and the buffering species is selected from the group of acetic acid, formic acid, N-morpholinoethane sulfonic acid, N-morpholinopropane sulfonic acid, tricine, triethanolamine, glycine, bicine, and histidine. Generally, the buffering species is titrated with HCl or NaOH.

Additionally, a preferred embodiment of the present invention includes a strong-acid cation exchange adsorbent selected from the group of TOSOHAAS S-5PW (Tosohass, Inc.), Bio-Gel MA7S (Bio-Rad Laboratories), S Sepharose Fast Flow (Pharmacia LKB Biotechnology), Zorbax Bioseries SCX (Du Pont), Mono-S (Pharmacia LKB Biotechnology), or POROS SCX (PerSeptive Biosystems); or a strong-base anion exchange adsorbent selected from the group of TOSOHAAS Q-5PW (Tosohaas, Inc.), Bio-Gel MA7Q (Bio-Rad Laboratories), Q Sepharose Fast Flow (Pharmacia LKB Biotechnology), Zorbax Bioseries SAX (Du Pont), Mono-Q (Pharmacia LKB Biotechnology), POROS SAX (PerSeptive Biosystems).

In a most preferred embodiment, the present invention includes a method of displacement chromatagraphy for the separation of proteins wherein when the chromatography column contains an anion exchange adsorbent, the buffering species in the presaturation buffer has a higher pKa than the elution buffer, and wherein when the chromatography column contains a cation exchange adsorbent, the buffering species in the presaturation buffer has a lower pKa than the elution buffer.

In another most preferred embodiment of the present invention, the elution buffer is composed of water and a buffering species titrated with a strong acid or base to an elution pH, the exchange adsorbent is packed into a tube consisting of stainless steel or glass, a high-performance liquid chromatography pump is used to pump fluids through said chromatagraphy column, and the detecting step is performed with a UV/Vis spectraphotometer.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

Figure 1:
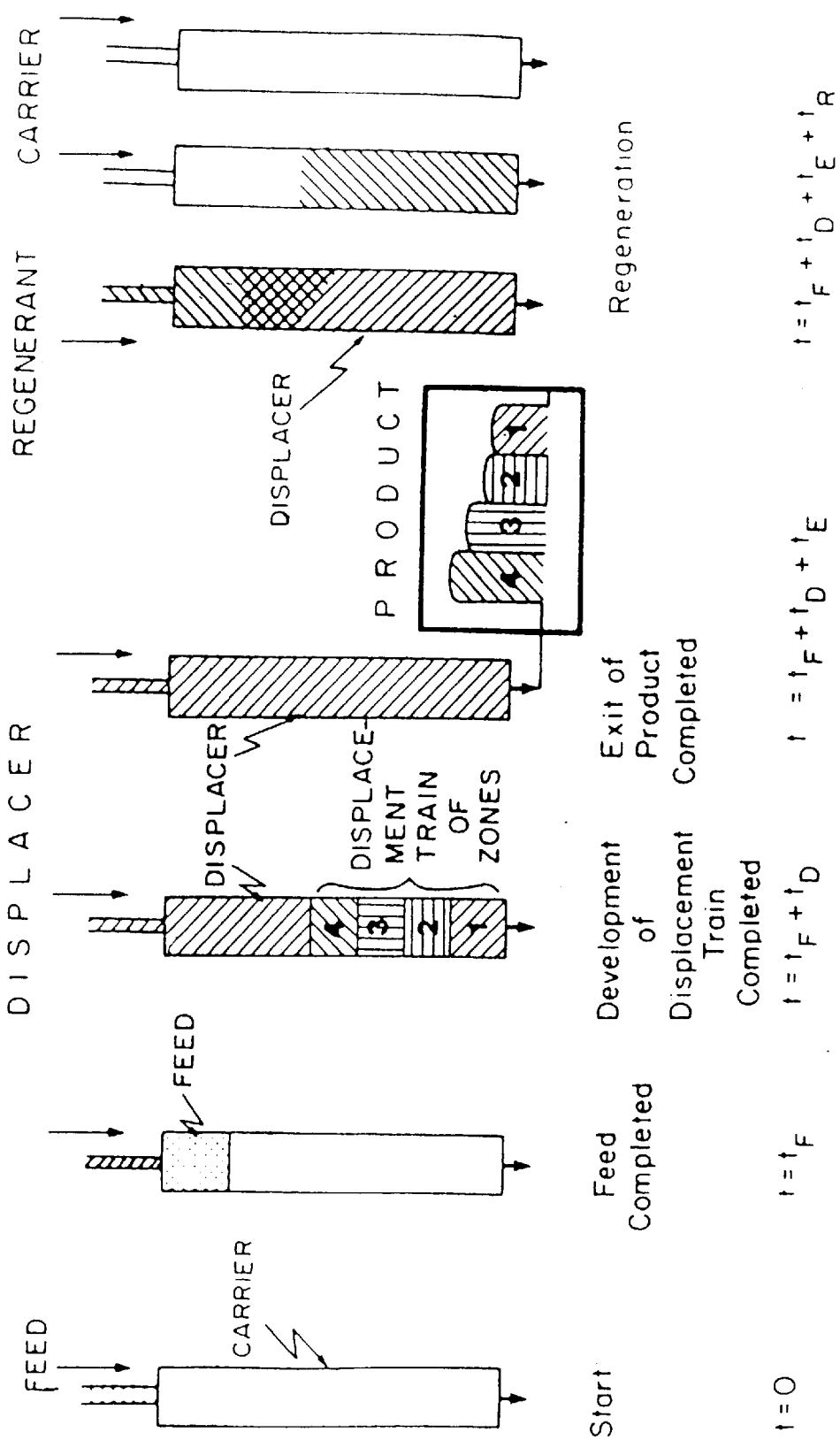
FIG. 1 depicts of the traditional process of displacement chromatography. Shown is a cycle of feed introduction, introduction of displacer, development of displacement train of zones, and the regeneration of the column (from Cs. Horvath, et al., *J. Chromatogr.* 255:273 (1983)).

It will be apparent to one skilled in the art that various substitutions and modifications may be made to the invention disclosed herein without departing from the scope and spirit of the invention.

As used herein, the term "chromatographic column" refers to a tube packed with adsorbent particles and used to perform chromatography.

As used herein, the term "solute" refers to the species to be separated, which are generally proteins.

As used herein, the term "displacement chromatography" refers to refers to a chromatographic method in which the solutes to b e separated form a contiguous sequence of rectangular bands abutted against each other in the column effluent.

As used herein, the terms "displacer" or "displacer component," refer to the component in traditional displacement chromatography which is dissolved in the solvent and perfused through the chromatographic column after the introduction of the feed slug in order to induce the development of a displacement train.

As used herein, the term "displacement pattern" refers to the solute concentration profiles in the column effluent, as a function of time, formed in displacement chromatography.

As used herein the term "displacement train" refers to the sequence of solute bands formed in displacement chromatography.

As used herein the term "mobile phase" refers to the fluid phase (generally a liquid) in the chromatographic column.

As used herein the term "feed slug" refers to a mixture of solutes to be separated together with a solvent, which is injected into the chromatographic column at the start of the operation.

As used herein the term "adsorbent" refers to the solid packing material inside the chromatographic column which selectively binds (i.e., adsorbs) one or more of the solutes to be separated. The adsorbent will generally be either a cation exchanger (which adsorbs cations) or an anion exchanger (which adsorbs anions).

As used herein the term "equilibrium adsorption properties" refers to the properties which determine the amount of a solute that is adsorbed onto the column packing as a function of the mobile phase composition.

As used herein the terms "pH gradient" or "pH profile" refer to the spatial variation in pH inside the chromatographic column.

As used herein, the terms "retained pH gradient " or "retained pH profile" refer to the spatial variation in pH inside the chromatographic column for the case where this variation travels more slowly that the velocity of an unretained (i.e., unadsorbed) tracer.

As used herein the term "adsorbed buffering species" refers to a buffering species (i.e., a weak acid or base such as acetic acid) where at least one of the charged forms of the buffering species is the appropriate charge type in order to participate in ion-exchange adsorption equilibrium with the adsorbent.

As used herein the term "protein band velocity wave" refers to the two-dimensional curve produced when the velocity through the chromatographic column of a solute band containing a trace amount of protein is plotted on the horizontal axis against the pH as which the band exists on the vertical axis.

As used herein the term "vertical section of pH profile" refers to the individual locations on the effluent pH profile from the chromatographic column where the pH changes rapidly. This rapid pH change starts at one constant pH region (i.e., a pH plateay) and finishes at another constant pH region.

As used herein the term "adsorption isotherm" refers to the relation between the concentration of solute in the mobile phase and the solute concentration in the fluid phase as a fixed temperature.

As used herein the term "intermediate pH plateau" refers to a region on the pH profile where the pH is constant. The first such plateau to exit in the column effluent during a chromatographic run is the "presaturation plateau," the last to exit is the "elution pH plateau," and the plateau between these two plateaus is the "intermediate pH plateau."

The present invention is directed to methods of displacement chromatography without using a displacer component, and instead using a retained pH gradient formed with properly-formulated presaturation and elution solvents containing appropriate buffer species.

It is contemplated additionally that the present invention provide a method of displacement chromotagraphy for the separation of proteins, comprising the steps of: presaturating a chromatography column by perfusing said chromatography column with a mixture of solvent and a buffering species titrated with a strong acid or strong base to a n appropriate presaturation pH, wherein said chromatography column is packed with either a strong-acid cation exchange adsorbent or strong-base anion exchange adsorbent; injecting a feed slug containing solutes to be separated into said chromatography column; perfusing said chromatography column with an appropriate elution buffer to produce a column effluent; detecting separated proteins in said column effluent; and collecting said separated proteins.

The object of the present invention is to provide a method for eliminating the use of a displacer in displacement chromatography. This is accomplished by producing an appropriate retained pH gradient using adsorbed buffering species. When the band velocity curves of the proteins under consideration intersect a vertical section of this pH profile, and none of these protein have adsorption isotherm which cross each other at the pH of the intermediate plateau, and when the amount of protein in the feed slug to the column is such that bands of the appropriate concentration are formed in the displacement train, then a displacement pattern results in a chromatography column even though no displacer is present.

The following examples are given for the purpose of illustrating various embodiments of the invention and are not meant to limit the present invention in any fashion:

EXAMPLE 1
"Displacerless" Displacement Chromatography

The novel technique of "displacerless" displacement chromatography builds upon work in the areas of displacement chromatography and chromatofocusing in order to develop a novel chromatographic technique for use in the biotechnology industry for the process-scale purification of proteins.

Figure 3:
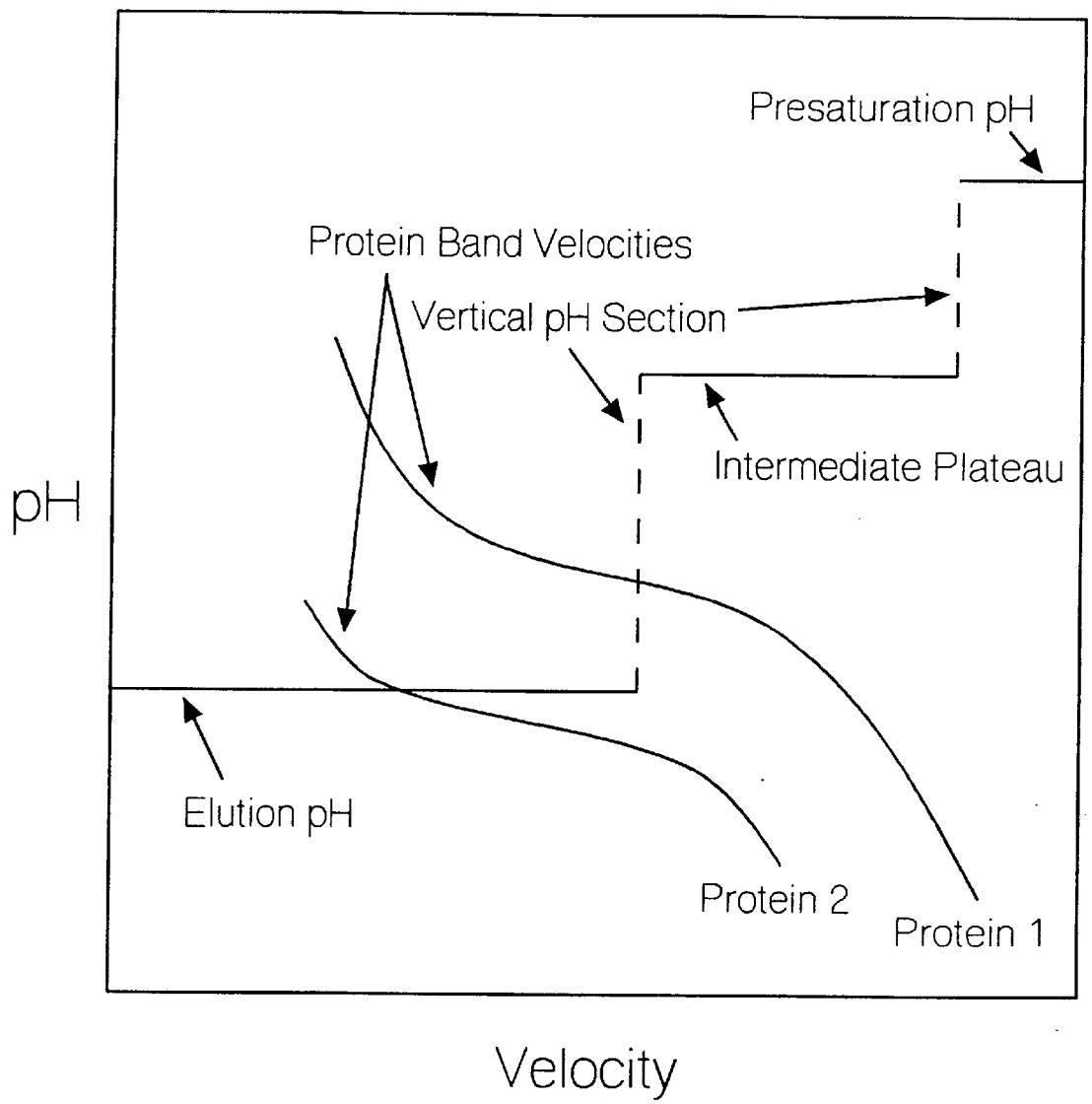
FIG. 3 recites graphically the criteria to be considered for focusing when a stepwise pH transition is present in a chromatography column.

Criteria for the focusing of protein bands in a retained pH gradient consisting of stepwise pH transitions has been developed previously (D. D. Frey, et al., *AIChE J.*, 41:1171 (1995); D. D. Frey, *Biotechnol. Progress,* 12:65 (1996)) and is illustrated graphically in FIG. 3. In particular, the figure illustrates the local-equilibrium behavior of a pH gradient in terms of the velocities of features on the pH profile. The particular pH gradient shown in the figure was produced by presaturating an anion-exchange column at an initial pH with a buffer containing a single buffering species, and eluting the column at a lower pH using a stepwise change to an elution buffer containing a different, single buffering species. As described by Frey et al., *AIChE J.,* 41:1171 (1995), under these conditions, a pH gradient is formed consisting of one unretained and one retained pH transition provided that both buffering species have ionic forms that are adsorbed by the column packing and the buffering species in the presaturation buffer has a lower acid-base dissociation constant (i.e., a higher $pK_a$) than the buffering species in the elution buffer. Also shown in the figure are the band velocity curves for two proteins; i.e., curves depicting the velocities of protein bands with trace concentrations as a function of pH.

As discussed by Frey, *Biotechnol. Progress,* 12:65 (1996), if the protein band velocity curve intersects a vertical section of the pH profile (as illustrated by protein 1 in FIG. 3), the protein experiences a focusing effect due to the fact that the protein band velocity downstream from the pH transition is less than the velocity of the transition, while the opposite situation applies upstream from the pH transition, so that the protein tends to collect at the transition itself. Conversely, when the protein band velocity curve intersects the pH profile on a plateau (as illustrated by protein 2 in FIG. 3), the protein becomes situated on the plateau and elutes from the column isocratically at that pH.

According to Strong and Frey (J. Strong and D. Frey, *J. Chromatogr.,* in press)), it is usually the case that the protein band velocity curve becomes relatively flat near the isoelectric point of the protein (see FIG. 1 of D. D. Frey, *Biotechnol. Progress,* 12:65 (1996)). Under these conditions, a buffer system appropriate for focusing a protein on a single, stepwise, retained pH transition can be selected using local-equilibrium theory to ensure that a retained pH transition spans a range which includes the isoelectric point of the protein under consideration. For the relatively simple case where the presaturation and elution buffers each contain a single, different, buffering species, this condition occurs when the pH of the elution buffer, and the pH that the presaturation buffer would have if the presaturation buffering species was present at the same molar concentration as the buffering species in the elution buffer, span the appropriate pH range (D. D. Frey, *Biotechnol. Progress,* 12:65 (1996)).

The main advantage of the technique is that an isotachic pattern of adjacent square-wave solute bands is produced in the column without using a "displacer" component during the development stage of the process. Instead, a retained pH gradient is employed using adsorbed buffering species. The purpose of the retained pH gradient is to cause a change in the adsorption equilibrium properties of the last (i.e., farthest upstream) protein to exit the column such that a rectangular protein band is produced for that protein. This farthest upstream protein band can in turn be utilized to displace any number of proteins using in effect the conventional mechanism of displacement development provided that those proteins have a lower affinity for the adsorbent in the intermediate pH plateau of the pH profile.

The retained pH gradient just described is produced using standard, readily-available buffering species which are generally harmless from the viewpoint of subsequent protein processing such that these components do not need to be removed from the purified protein sample. It is important to recognize that the eluting buffering species does not act like a traditional displacer in this process, i.e., it is unnecessary for this buffering species to have its adsorption isotherm overlie that of the proteins to be displaced. Instead, the presence of a retained pH gradient associated with a change in buffer composition produces a rectangular protein band for the farthest upstream protein.

Figure 2:
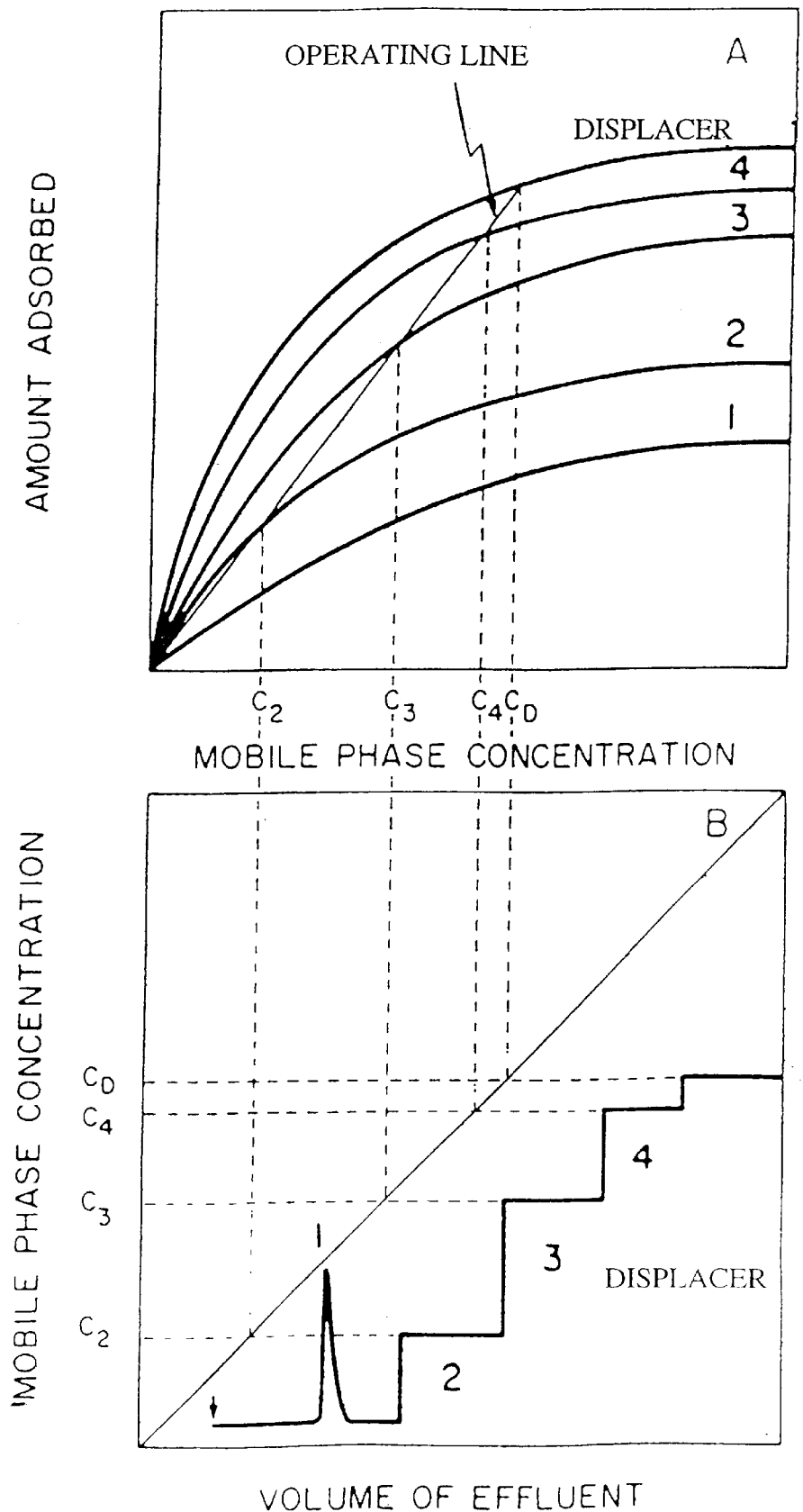
FIG. 2 shows the relationship between the adsorption isotherms needed for traditional displacement chromatography (from Cs. Horvath, et al., *J. Chromatogr.* 255:273 (1983)).
Figure 4:
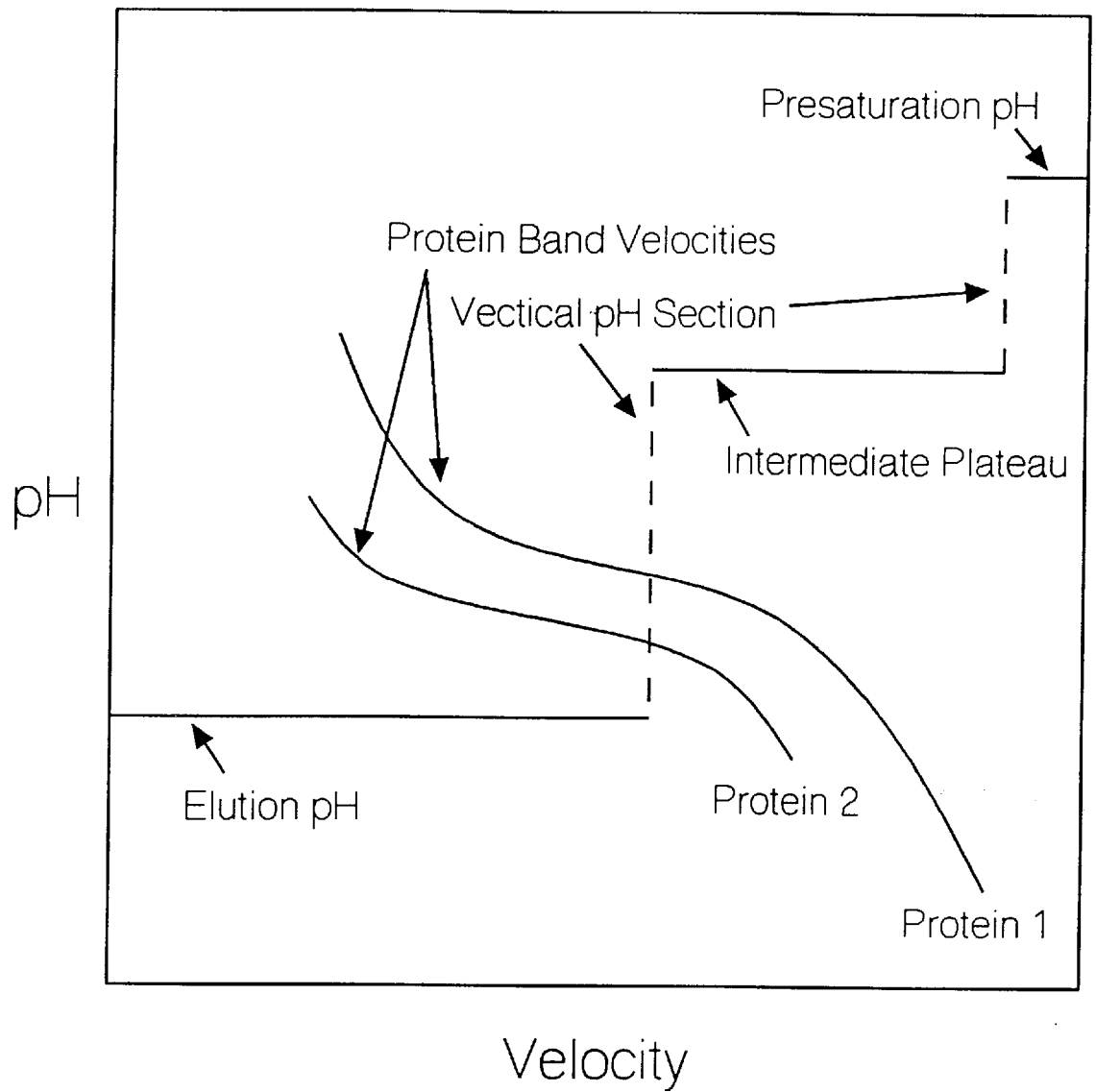
FIG. 4 illustrates the relationship between the band velocity curves of two solutes (proteins) and the velocity of a stepwise pH transition in order for displacerless displacement to occur for the two solutes.

In order to apply the technique of displacerless displacement chromatography, a chromatofocusing system must be designed by the proper selection of buffering species in the elution and presaturation buffers, and by the proper selection of the adsorbent, so that all of the proteins which are to appear in the displacement pattern have trace band velocity curves which intersect a single stepwise change in pH, as shown in FIG. 4. In addition, on the downstream side of the pH transition (i.e., on the intermediate pH plateau), the adsorption isotherms must possess the relation shown in FIG. 2; i.e., each isotherm must have a convex shape, with none of the isotherms crossing each other. Finally, the amount of protein in the feed slug must be high enough to produce high enough concentrations in the resulting displacement train so that, on the intermediate plateau, a step change in concentration from the zero level to the level in the protein band will have the same velocity as the retained pH gradient. If these three conditions are met, a displacement train of solutes is formed, as demonstrated theoretically and experimentally below.

EXAMPLE 2

Numerical Simulations

Figure 5:
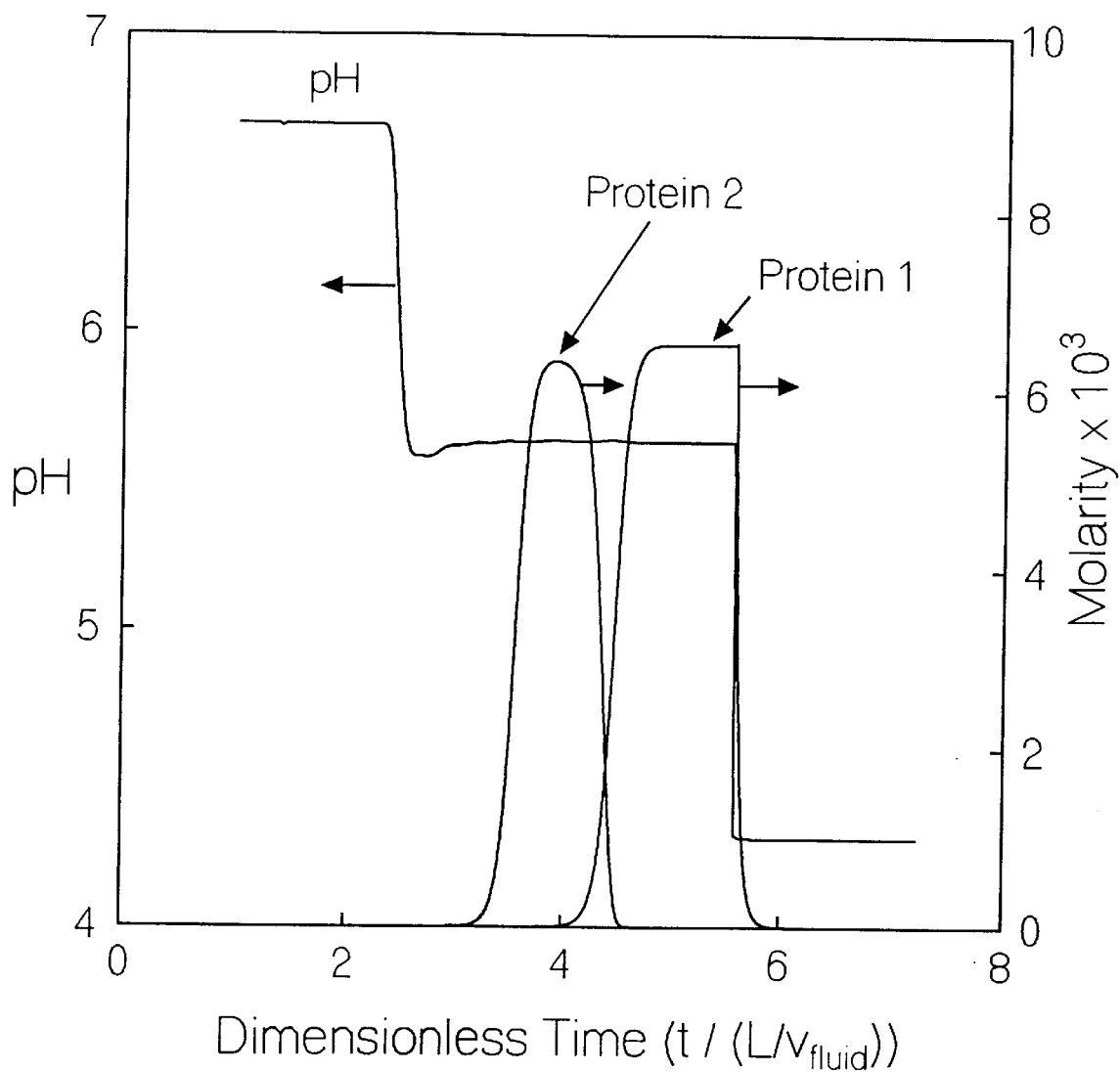
FIG. 5 shows the numerical simulation of the displacerless displacement chromatography of two proteins. Conditions are described in the specification at Example 2.

FIG. 5 illustrates a numerical simulation of the proposed process. The simulation shown was performed using numerical methods discussed by Frey et al., *AIChE J.*, 41:1171 (1995). The physical properties for the two proteins were chosen as follows: isoelectric points were 4.5 and 4.0; the characteristic charge for binding was 2.2 times the difference between the existing pH and the isoelectric point; the total number of absorbent sites overlaid per protein molecule: 200. The meaning of these physical properties would be generally known to those skilled in the art. A 90-$\mu$m diameter strong-base ion exchange adsorbent with an adsorption capacity of 0.35 mol/liter was employed for the simulations and, under the conditions shown, the various criteria for forming an isotachic displacement pattern were satisfied; i.e., the band velocity curves of the two proteins intersected a single stepwise pH transition, and the adsorption isotherms for the two proteins exhibited the relationship shown in FIG. 2. The proper pH profile was attained by presaturating the column with 0.05M NaOH titrated with acetic acid to pH 4.2, and eluting the column with 0.05M NaOH titrated with N-morpholinoethane sulfonic acid to pH 6.7. The column length was 15 cm, its diameter was 1 cm, and the flow rate in the column was 0.8 cm$^3$/min. 270 mg of total protein were injected into the column in a 8 ml feed slug. As illustrated, under these conditions the proteins form a displacement train even though no displacer component is employed.

EXAMPLE 3

Experimental Verification

Experiments were performed in order to verify the operation of the "displacerless" displacement chromatography technique. These experiments were performed using 10-$\mu$m strong-base, anion-exchange particles (TOSOHAAS Q-5PW, Tosohaas Inc.) composed of cross-linked polystyrene with quaternary amine groups. These particles were packed into a stainless steel column which had an internal diameter of 7.5 mm and a length of 7.5 cm. A ThermoSeparation Products SpectraSYSTEM P4000 pump was used to deliver the solvent, and a ThermoSeparation Products SpectraSYSTEM UV2000 UV/Vis detector monitored the absorbance of the column effluent in order to determine the presence of protein. A Sensorex sealed combination pH minielectrode, seated in an in-line flow cell and connected to an Orion Research Model 701A Ionalyzer, monitored the solvent pH. The analog outputs of the Ionalyzer and UV/Vis detector were directed to a Strawberry Tree Datashuttle, which was connected to an 80286-based IBM PS/2 computer running Strawberry Tree Workbench data acquisition software.

Displacerless displacement experiments were performed by equilibrating the column with the presaturating buffer until the column effluent reached the presaturation pH. After equilibration, a protein feed slug was loaded into the sample loop of a Rheodyne injection valve, and the solvent was switched to the eluent buffer while the protein sample was simultaneously introduced onto the column. The column effluent was monitored at 280 nm in all experiments. Fractions collected from the column were analyzed using a Synchrom Q300 strong anion exchange column. A standard salt gradient was used for the analytical column.

Figure 6:
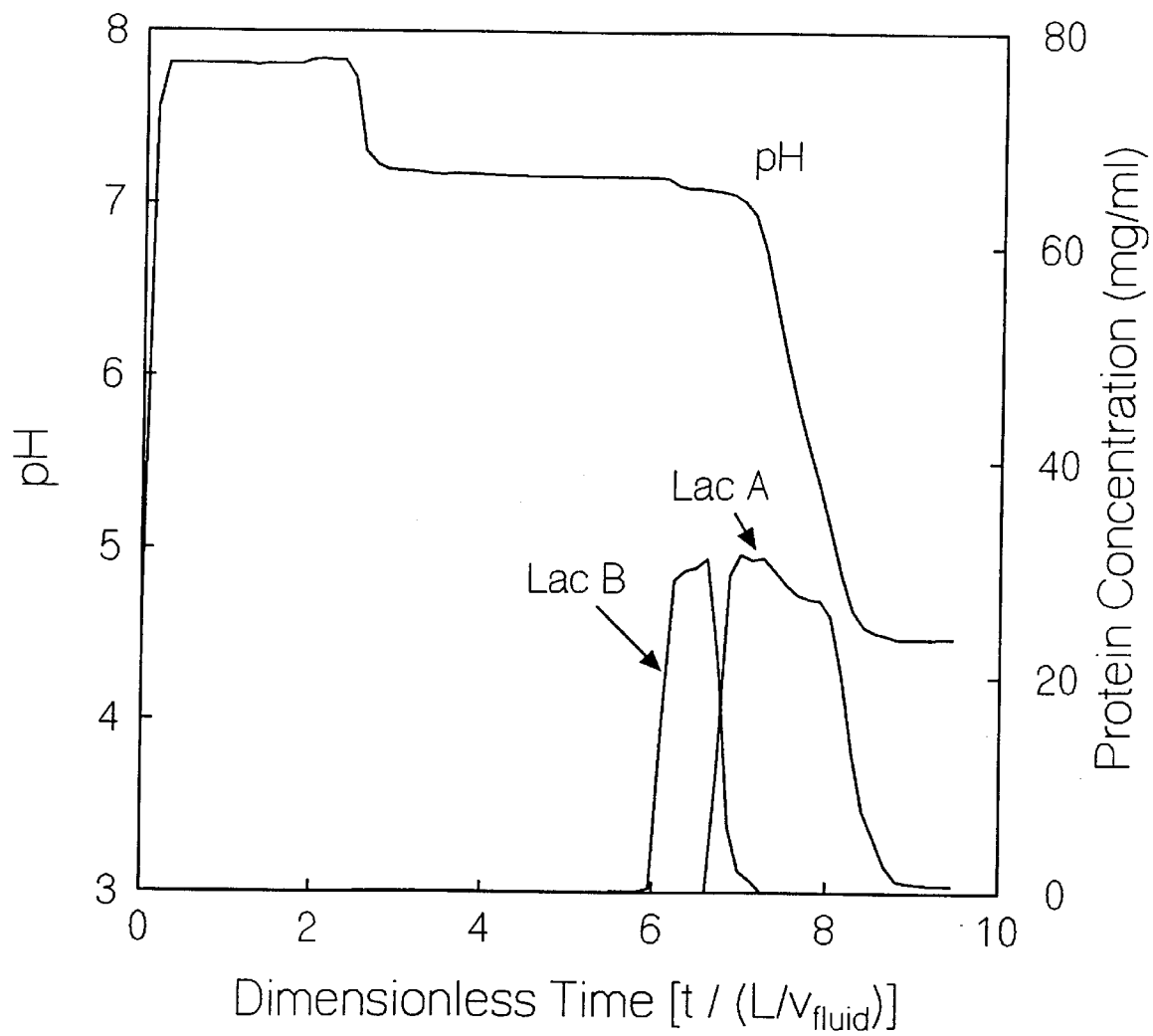
FIG. 6 shows the experimental results for the displacerless displacement chromatography of β-Lactoglobulin A and B. Conditions are described in the specification at Example 3.
Figure 7:
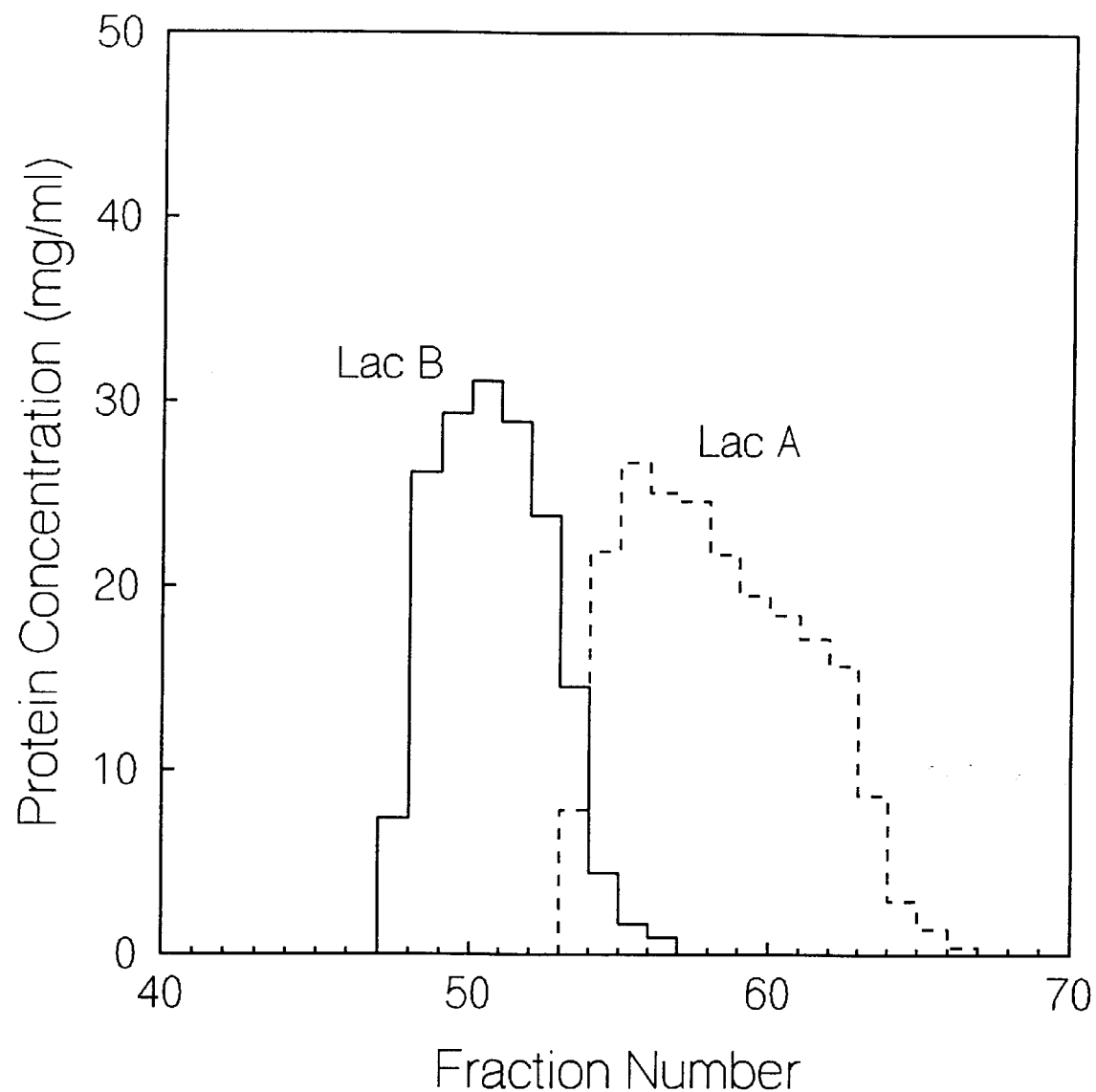
FIG. 7 resports the analysis of the individual fractions collected from the experiment shown in FIG. 6.

To obtain the experimental results shown in FIGS. 6 and 7, the anion-exchange column was presaturated with 0.03M NaOH titrated with acetic acid to a pH of 4.5, and eluted at a flow rate of 0.15 cm$^3$/min with 0.03M NaOH titrated with N-morpholinopropane sulfonic acid (MOPS) to a pH of 7.8. 100 mg of a mixture of $\beta$-Lactoglobulin A and B in a 5 ml feed slug were injected into the column between the elution and presaturation steps. This produced a retained pH gradient that intersected the band velocity curves of both the A and B forms of $\beta$-Lactoglobulin. As shown, the more strongly adsorbed protein (the A form) produced a rectangular solute band that then displaced the B form of $\beta$-Lactoglobulin. Both proteins were separated in the column effluent.

Any patents or publications mentioned in this specification are indicative of the levels of those skilled in the art to which the invention pertains. Further, these patents and publications are incorporated b y reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of displacement chromatography for the separation of proteins, comprising the steps of:

selecting an adsorbed buffering species to produce an appropriate retained pH gradient having a pH profile, wherein band velocity curves of proteins to be separated intersect a vertical section of said pH profile, wherein all adsorption isotherms of said proteins to be separated are convex, and wherein none of said proteins to be separated have an adsorption isotherm which crosses another of said proteins' adsorption isotherm at a pH of an intermediate plateau; and supplying an amount of said proteins to be separated in a feed slug to produce high enough concentrations of said proteins to result in a displacement train, that, on said intermediate pH plateau, a step change in concentration from a zero level to a level in a protein band has a same velocity as a retained pH gradient.

2. A method of displacement chromatography for the separation of proteins, comprising the steps of:

presaturating a chromatography column by perfusing said chromatography column with a mixture of solvent and a buffering species titrated with a strong acid or strong base to an appropriate presaturation pH, wherein said chromatography column is packed with either a strong-acid cation exchange adsorbent or strong-base anion exchange adsorbent;

injecting a feed slug containing solutes to be separated into said chromatography column;

perfusing said chromatography column with an appropriate elution buffer to produce a column effluent;

detecting separated proteins in said column effluent; and collecting said separated proteins.

3. The method of displacement chromatography for the separation of proteins of claim 2, wherein said solvent is water.

4. The method of displacement chromatography for the separation of proteins of claim 2, wherein said buffering species are selected from the group of acetic acid, formic acid, N-morpholinoethane sulfonic acid, N-morpholinopropane sulfonic acid, tricine, triethanolamine, glycine, bicine, and histidine.

5. The method of displacement chromatography for the separation of proteins of claim 2, wherein said strong acid is HCl.

6. The method of displacement chromatography for the separation of proteins of claim 2, wherein said strong base is NaOH.

7. The method of displacement chromatography for the separation of proteins of claim 2, wherein when said chromatography column contains an anion exchange adsorbent, said buffering species in said presaturation buffer has a higher pKa than said elution buffer, and wherein when said chromatography column contains a cation exchange adsorbent, said buffering species in said presaturation buffer has a lower pKa than said elution buffer.

8. The method of displacement chromatography for the separation of proteins of claim 2, wherein said elution buffer is composed of water and a buffering species titrated with a strong acid or base to an elution pH.

9. The method of displacement chromatography for the separation of proteins of claim 2, wherein said exchange adsorbent is packed into a tube consisting of stainless steel or glass.

10. The method of displacement chromatography for the separation of proteins of claim 2, wherein a high-performance liquid chromatography pump is used to pump fluids through said chromatography column.

11. The method of displacement chromatography for the separation of proteins of claim 2, wherein said detecting step is performed with a UV/Vis spectraphotometer.

* * * * *